United States Patent
Ono et al.

(10) Patent No.: US 7,045,517 B2
(45) Date of Patent: *May 16, 2006

(54) TRIAZINE COMPOUNDS

(75) Inventors: M. Ono, Lexington, MA (US); Lijun Sun, Harvard, MA (US); Shijie Zhang, Nashua, NH (US); Teresa Przewloka, Burlington, MA (US); David A. James, Cambridge, MA (US); Wenli Ding, Worcester, MA (US); Yumiko Wada, Waltham, MA (US)

(73) Assignee: Synta Pharmaceuticals Corp., Lexington, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/656,360

(22) Filed: Sep. 5, 2003

(65) Prior Publication Data

US 2004/0053926 A1 Mar. 18, 2004

Related U.S. Application Data

(63) Continuation of application No. 10/006,624, filed on Nov. 30, 2001, now Pat. No. 6,680,315, which is a continuation-in-part of application No. 09/594,362, filed on Jun. 15, 2000, now Pat. No. 6,384,032.

(51) Int. Cl.
| | | |
|---|---|---|
| A61K 31/53 | (2006.01) | |
| A61P 3/10 | (2006.01) | |
| A61P 17/06 | (2006.01) | |
| A61P 19/02 | (2006.01) | |
| A61P 25/28 | (2006.01) | |

(52) U.S. Cl. ........................ 514/227.8; 514/231.5; 514/241; 544/197; 544/198; 544/206; 544/207; 544/219; 544/111; 544/59

(58) Field of Classification Search ............. 514/241, 514/227.8, 231.5
See application file for complete search history.

(56) References Cited

U.S. PATENT DOCUMENTS

| 3,549,757 A | 12/1970 | Kodama et al. | 424/248 |
| 4,033,957 A * | 7/1977 | Hofer et al. | 260/246 |
| 5,258,513 A * | 11/1993 | Van Keulen et al. | 544/58.2 |
| 6,384,032 B1 * | 5/2002 | Ono et al. | 514/241 |

FOREIGN PATENT DOCUMENTS

| DE | 23 32 597 | 6/1973 |
| DE | 2332597 A1 | 1/1975 |
| FR | 2 236 126 | 4/1974 |
| FR | 2236126 | 1/1975 |
| WO | 99/36410 | 7/1999 |

OTHER PUBLICATIONS

Goghari et al. J. Inst. Chem. 48(2) 77-79, 1976.*
Goghari et al. J. Indian Chem. Soc. 53(2) 207-208, 1976.*
Goghari et al. J. Inst. Chem. Calcutta, 48 (2), 77-9, 1976. CA 86: 43668, 1977.*
Goghari et al. J. Indian Chemi. Soc. Chem. 53 (2), 207-8, 1976. CA 85: 32961 1976.*
Pandya et al., "s-Triazinyl Derivatives As Medicinal Agents", J. Inst. Chemists (India), vol. XLVIII, Sep., 1976 pp. 245-247.
Pandya et al., "Studies On Potential Drugs:Potential Anthelmintics Part I", J. Inst. Chemists (India), vol. XLVII, Nov., 1975, pp. 235-237.
Azev et al.., "Synthesis And Biological Activity Of Cyanomethoxy-s-Triazines", Translated from Khimiko-Farmatsevticheskii Zhurnal, vol. 25, No. 10, pp. 43-46, Oct., 1991.

(Continued)

Primary Examiner—Venkataraman Balasubramanian
(74) Attorney, Agent, or Firm—Edwards & Angell, LLP; Jeffrey D. Hsi

(57) ABSTRACT

This invention relates to triazine compounds of formula (I):

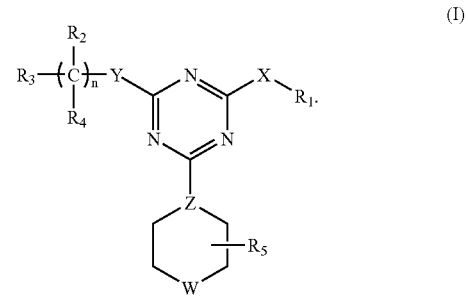

$R_1$ is, aryl,

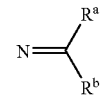

or heteroaryl; each of $R_2$, $R_4$, and $R_5$, independently, is $R^c$, halogen, nitro, nitroso, cyano, azide, isothionitro, $SR^c$, or $OR^c$; $R_3$ is $R^c$, alkenyl, alkynyl, aryl, heteroaryl, cyclyl, heterocyclyl, $OR^c$, $OC(O)R^c$, $SO_2R^c$, $S(O)R^c$, $S(O_2)NR^cR^d$, $SR^c$, $NR^cR^d$, $NR^cCOR^d$, $NR^cC(O)OR^d$, $NR^cC(O)NR^cR^d$, $NR^cSO_2R^d$, $COR^c$, $C(O)OR^c$, or $C(O)NR^cR^d$; n is 0, 1, 2, 3, 4, 5, 6, or 7; X is O, S, S(O), $S(O_2)$, or $NR^c$; Y is a covalent bond, $CH_2$, C(O), C=N—$R^c$, C=N—$OR^c$, C=N—$SR^c$, O, S, S(O), or $S(O_2)$; Z is N; and W is O, S, S(O), $S(O_2)$, $NR^c$, or $NC(O)R^c$; in which each of $R^a$ and $R^b$, independently, is H, alkyl, aryl, heteroaryl; and each of $R^c$ and $R^d$, independently, is H, alkyl, or alkylcarbonyl.

53 Claims, No Drawings

OTHER PUBLICATIONS

Jelene et al., "Synthesen von substituierten 1,3.5-Triazinen and über eine neuartige Synthese substituierter s-Triazolo [4.3-a]", Monatshefte Für Chemie, 1966, pp. 1714-1722.

Pearlman et al., The Journal of the American Chemical Society, vol. LXXI, Jan.-Apr. 1949, pp. 1128-1129.

Chemical Abstracts, "Alkoxy-s-triazines. II", Abs No. 172619t, vol. 82, Jun., 1975, p. 91.

Chemical Abstracts, Abs Nos. 14188k; 141882d; 141884f; 141885g and 141887j., vol. 74, Jun., 1971, p. 601.

BE 660,634 A (Badische Anilin & Soda Fabrik A.-G.) Sep. 6, 1965, see pp. 6-7, example 3.

Trinchieri, G. "Function and Clinical use of Interleukin-12." Curr. Opin. Hematol. Jan. 1997, vol. 4, No. 1, pp. 59-66.

Pandya et al., "s-Triazinyl Derivatives As Medicinal Agents", J. Inst. Chemists (India), vol. XLVIII—Part I, Jan. 1976, pp. 245-247.

Pandya et al., "Studies On Potential Drugs:Potential Anthelmintics Part I", J. Inst. Chemists (India), vol. XLVII, Nov., 1975, pp. 235-237.

Azev et al.., "Synthesis And Biological Activity Of Cyanomethoxy-s-Triazines", Translated from Khimiko-Farmatsevticheskii Zhurnal, vol. 25, No. 10, pp. 43-46, Oct., 1991.

Jelene et al., "Synthesen von substituierten 1,3.5-Triazinen and über eine neuartige Synthese substituierter s-Triazolo [4.3-a]", Monatshefte Für Chemie, 1966, pp. 1714-1722.

Pearlman et al., "Alkoxy-s-triazines. II", The Journal of the American Chemical Society, vol. LXXI, Jan.-Apr. 1949, pp. 1128-1129.

Chemical Abstracts, No. 172619t, vol. 82, No. 25, Jun., 1975, p. 91.

Chemical Abstracts, Nos. 14188k; 141882d; 141884f; 141885g and 141887j., vol. 74, No. 25, Jun. 1971, p. 601.

BE 660,634 A (Badische Anilin & Soda Fabrik A.-G.) Sep. 6, 1965, see pp. 6-7, example 3.

Trinchieri, G., "Function and clinical use of interleukin-12." Curr. Opin. Hematol., vol. 4, No. 1, Jan. 1997, pp. 59-66.

International Search Report dated Jun. 12, 2003.

* cited by examiner

TRIAZINE COMPOUNDS

RELATED APPLICATIONS

Pursuant to 35 U.S.C. § 120, this application is a continuation of prior U.S. application Ser. No. 10/006,624, filed on Nov. 30, 2001, now U.S. Pat. No. 6,680,315, which is a continuation-in-part of prior U.S. application Ser. No. 09/594,362, filed on Jun. 15, 2000, now U.S. Pat. No. 6,384,032. The contents of both of these prior applications is incorporated herein by reference in its entirety.

BACKGROUND

Interleukin-12 (IL-12) is a heterodimeric cytokine (p70) composed of two subunits (p35 and p40), and plays key roles in immune responses by bridging innate resistance and antigen-specific adaptive immunity. Trinchieri (1993) *Immunol Today* 14: 335. For example, it promotes type 1 T helper cell (Th1) responses and, hence, cell-mediated immunity. Chan et al. (1991) *J Exp Med* 173: 869; Seder et al. (1993) *Proc Natl Acad Sci USA* 90: 10188; Manetti et al. (1993) *J Exp Med* 177: 1199; and Hsieh et al. (1993) *Science* 260: 547. Overproduction of IL-12 causes excessive Th1 responses, and may result in inflammatory disorders, insulin-dependent diabetes mellitus, multiple sclerosis, rheumatoid arthritis, psoriasis, Crohn's disease, or sepsis. See, for example, Gately et al. (1998) *Annu Rev Immunol.* 16: 495; and Abbas et al. (1996) *Nature* 383: 787. Thus, inhibiting IL-12 overproduction is an approach to treat the just-mentioned diseases. Trembleau et al. (1995) *Immmunol. Today* 16: 383; and Adorini et al. (1997) *Chem. Immunol.* 68: 175. For example, overproduction of IL-12 and the resultant excessive Th1 type responses can be suppressed by modulating IL-12 production. A compound that down-regulates IL-12 production can be used for treating inflammatory diseases. Ma et al. (1998) *Eur Cytokine Netw* 9: 54.

SUMMARY

This invention is based on the identification of new compounds from a library of 80,000 compounds, which were screened for their abilities to inhibit IL-12 overproduction. In one aspect, this invention features triazine compounds of formula (I)

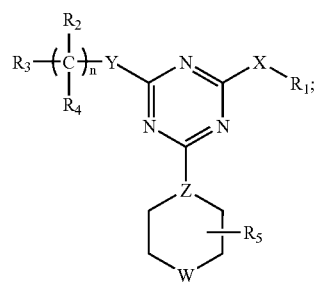

wherein $R_1$ is

[referred to hereinafter as $NC(R^aR^b)$], aryl, or heteroaryl; each of $R_2$, $R_4$, and $R_5$, independently, is $R^c$, halogen, nitro, nitroso, cyano, azide, isothionitro, $SR^c$, or $OR^c$; $R_3$ is $R^c$, alkenyl, alkynyl, aryl, heteroaryl, cyclyl, heterocyclyl, $OR^c$, $OC(O)R^c$, $SO_2R^c$, $S(O)R^c$, $S(O_2)NR^cR^d$, $SR^c$, $NR^cR^d$, $NR^c$-$COR^d$, $NR^cC(O)OR^d$, $NR^cC(O)NR^cR^d$, $NR^cSO_2R^d$, $COR^c$, $C(O)OR^c$, or $C(O)NR^cR^d$; n is 0, 1, 2, 3, 4, 5, 6, or 7; X is O, S, S(O), S(O$_2$), or $NR^c$; Y is a covalent bond, $CH_2$, C(O), C=N—$R^c$, C=N—$OR^c$, C=N—$SR^c$, O, S, S(O), or S(O$_2$); Z is N; and W is O, S, S(O), S(O$_2$), $NR^c$, or $NC(O)R^c$; in which each of $R^a$ and $R^b$, independently, is H, alkyl, aryl, heteroaryl; and each of $R^c$ and $R^d$, independently, is H, alkyl, or alkylcarbonyl. Note that the left atom shown in any substituted group described above is closest to the tirazine ring. Also note that when n is 2 or greater, the just-described triazine compound may have two or more different $C(R^2R^4)$ moieties. The same rule applies to other similar situations.

Referring to formula (I), a subset of the triazine compounds of this invention is featured by that $R^1$ is $NC(R^aR^b)$. In these compounds, W can be O; $R_5$ can be H or alkyl; X can be $NR^c$; $R^c$ can be H, methyl, ethyl, or acetyl; Y can be O or $CH_2$, and n can be 0, 1, 2, 3, or 4. In some embodiments, $R_3$ is aryl, heteroaryl (e.g., pyridinyl), $OR^c$, $SR^c$, $C(O)OR^c$, or $C(O)NR^cR^d$. In other embodiments, $R_3$ is

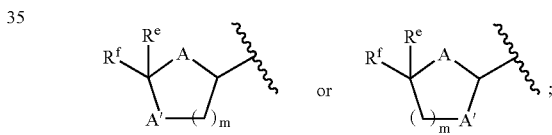

in which each of A and A', independently, is O, S, or NH; each of $R^e$ and $R^f$, independently, is H, alkyl, aryl, or heteroaryl; and m is 1 or 2.

In this subset of triazine compounds, $R^a$ or $R^b$, preferably, is

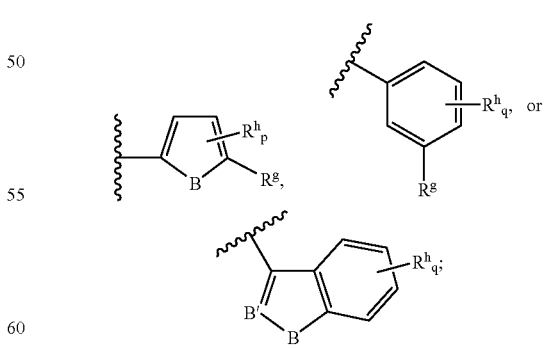

in which B is $NR^i$, O, or S; B' is N or $CR^i$; $R^g$ is H, alkyl, or alkoxyl; $R^h$ is halogen, CN, hydroxyl, alkyl, aryl, heteroaryl, alkoxyl, aryloxyl, or heteroaryloxyl; $R^i$ is H, alkyl, or alkylcarbonyl; p is 0, 1, or 2; and q is 0, 1, 2, 3, or 4. Preferably, B is $NR^i$; B' is CH; $R^g$ is H, methyl, ethyl, methoxy, or ethoxy; $R^h$ is F, Cl, CN, methoxy, methyl, or ethoxy; $R^i$ is H, methyl, ethyl, or acetyl; and q is 0, 1, or 2.

Another subset of the triazine compounds of this invention is featured by that $R^l$ is aryl or heteroaryl. In these compounds, W can be O; $R_5$ can be H or alkyl; X can be $NR^c$; $R^c$ can be H, methyl, ethyl, or acetyl; Y can be O or $CH_2$, and n can be 0, 1, 2, 3, or 4. In some embodiments, $R_3$ is aryl, heteroaryl (e.g., pyridinyl), $OR^c$, $SR^c$, $C(O)OR^c$, or $C(O)NR^cR^d$. In other embodiments, $R_3$ is

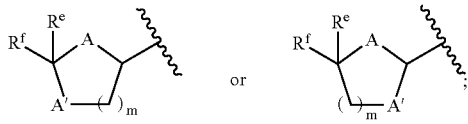

in which each of A and A', independently, is O, S, or NH; each of $R^e$ and $R^f$, independently, is H, alkyl, aryl, or heteroaryl; and m is 1 or 2.

In this second subset of triazine compounds, $R_1$, preferably, is

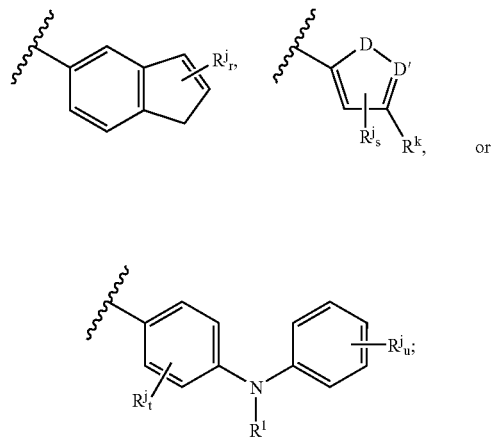

in which D is O, S, or $NR^m$; D' is N or $CR^m$; $R^j$ is halogen, CN, hydroxyl, alkyl, aryl, heteroaryl, alkoxyl, aryloxyl, or heteroaryloxyl; $R^k$ is aryl or hetereoaryl; $R^l$ is H, alkyl, or alkylcarbonyl; $R^m$ is H, alkyl, or alkylcarbonyl; r is 0, 1, or 2; s is 0 or 1; t is 0, 1, 2, 3, or 4; and u is 0, 1, 2, 3, 4, or 5. Preferably, $R_l$ is

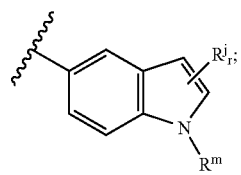

and $R^j$ is methyl, ethyl, propyl, or benzyl; and r can be 1 or 2.

In another aspect, this invention also features triazine compounds of formula (I), wherein $R_1$ is $NC(R^aR^b)$, aryl, or heteroaryl; each of $R_2$, $R_4$, and $R_5$, independently, is $R^c$, halogen, nitro, nitroso, cyano, azide, isothionitro, $SR^c$, or $OR^c$; $R_3$ is $R^c$, alkenyl, alkynyl, aryl, heteroaryl, cyclyl, heterocyclyl, $OR^c$, $OC(O)R^c$, $SO_2R^c$, $S(O)R^c$, $S(O_2)NR^cR^d$, $SR^c$, $NR^cR^d$, $NR^cCOR^d$, $NR^cC(O)OR^d$, $NR^cC(O)NR^cR^d$, $NR^cSO_2R^d$, $COR^c$, $C(O)OR^c$, or $C(O)NR^cR^d$; n is 0, 1, 2, 3, 4, 5, 6, or 7; X is O, S, S(O), S(O$_2$), or $NR^c$; Y is a covalent bond, $CH_2$, C(O), C=N—$R^c$, C=N—$OR^c$, C=N—$SR^c$, O, S, S(O), S(O$_2$), or $NR^c$; Z is CH; and W is O, S, S(O), S(O$_2$), $NR^c$, or $NC(O)R^c$; in which each of $R^a$ and $R^b$, independently, is H, alkyl, aryl, heteroaryl; and each of $R^c$ and $R^d$, independently, is H, alkyl, or alkylcarbonyl. A subset of the triazine compounds is featured by that $R^l$ is $NC(R^aR^b)$; and another subset is featured by that $R^l$ is aryl or heteroaryl.

Alkyl, alkenyl, alkynyl, aryl, heteroaryl (e.g., pyridinyl), cyclyl, heterocyclyl mentioned herein include both substituted and unsubstituted moieties. The term "substituted" refers to one or more substituents (which may be the same or different), each replacing a hydrogen atom. Examples of substituents include, but are not limited to, halogen, hydroxyl, amino, alkylamino, arylamino, dialkylamino, diarylamino, cyano, nitro, mercapto, carbonyl, carbamido, carbamyl, carboxyl, thioureido, thiocyanato, sulfoamido, $C_1$~$C_6$ alkyl, $C_1$~$C_6$ alkenyl, $C_1$~$C_6$ alkoxy, aryl, heteroaryl, cyclyl, heterocyclyl, wherein alkyl, alkenyl, alkoxy, aryl, heteroaryl cyclyl, and heterocyclyl are optionally substituted with $C_1$~$C_6$ alkyl, aryl, heteroaryl, halogen, hydroxyl, amino, mercapto, cyano, or nitro. The term "aryl" refers to a hydrocarbon ring system having at least one aromatic ring. Examples of aryl moieties include, but are not limited to, phenyl, naphthyl, and pyrenyl. The term "heteroaryl" refers to a hydrocarbon ring system having at least one aromatic ring which contains at least one heteroatom such as O, N, or S. Examples of heteroaryl moieties include, but are not limited to, furyl, fluorenyl, pyrrolyl, thienyl, oxazolyl, imidazolyl, thiazolyl, pyridinyl, pyrimidinyl, quinazolinyl, and indolyl.

Set forth below are exemplary compounds (Compounds 1–2) of this invention:

Compound 1

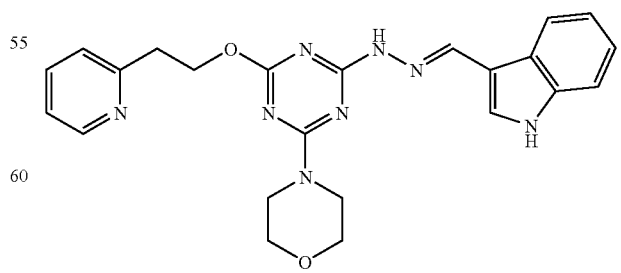

Compound 2

Compound 3

Compound 4

Compound 5

Compound 6

Compound 7

Compound 8

Compound 9

Compound 10

Compound 11

-continued

Compound 12

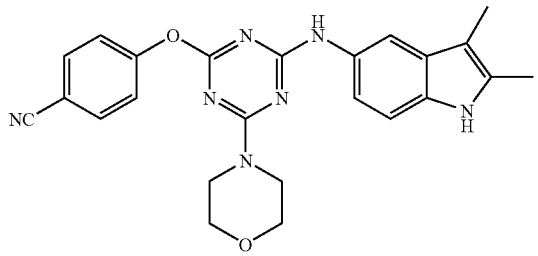

In still another aspect, this invention features a pharmaceutical composition that contains a pharmaceutically acceptable carrier and an effective amount of at least one of the above-described triazine compounds.

In further another aspect, the present invention features a method for treating an IL-12 overproduction-related disorder (e.g., rheumatoid arthritis, sepsis, Crohn's disease, multiple Sclerosis, psoriasis, or insulin-dependent diabetes). The method includes administering to a subject in need thereof an effective amount of a triazine compound of formula (I), wherein $R_1$ is $NC(R^aR^b)$, aryl, or heteroaryl; each of $R_2$, $R_4$, and $R_5$, independently, is $R^c$, halogen, nitro, nitroso, cyano, azide, isothionitro, $SR^c$, or $OR^c$; $R_3$ is $R^c$, alkenyl, alkynyl, aryl, heteroaryl, cyclyl, heterocyclyl, $OR^c$, $OC(O)R^c$, $SO_2R^c$, $S(O)R^c$, $S(O_2)NR^cR^d$, $SR^c$, $NR^cR^d$, $NR^cCOR^d$, $NR^c$-$C(O)OR^{d, NR^c}C(O)NR^cR^d$, $NR^cSO_2R^d$, $COR^c$, $C(O)OR^c$, or $C(O)NR^cR^d$; n is 0, 1, 2, 3, 4, 5, 6, or 7; X is O, S, S(O), $S(O_2)$, or $NR^c$; Y is a covalent bond, $CH_2$, C(O), C=N—$R^c$, C=N—$OR^c$, C=N—$SR^c$, O, S, S(O), $S(O_2)$, or $NR^c$; Z is N or CH; and W is O, S, S(O), $S(O_2)$, $NR^c$, or $NC(O)R^c$; in which each of $R^a$ and $R^b$, independently, is H, alkyl, aryl, heteroaryl; and each of $R^c$ and $R^d$, independently, is H, alkyl, or alkylcarbonyl.

The triazine compounds described above include the compounds themselves, as well as their salts and their prodrugs, if applicable. The salts, for example, can be formed between a positively charged substituent (e.g., amino) on a compound and an anion. Suitable anions include, but are not limited to, chloride, bromide, iodide, sulfate, nitrate, phosphate, citrate, methanesulfonate, trifluoroacetate, and acetate. Likewise, a negatively charged substituent (e.g., carboxylate) on a compound can form a salt with a cation. Suitable cations include, but are not limited to, sodium ion, potassium ion, magnesium ion, calcium ion, and an ammonium cation such as teteramethylammonium ion. Examples of prodrugs include esters and other pharmaceutically acceptable derivatives, which, upon administration to a subject, are capable of providing the triazine compounds described above.

In addition, some of the just-described triazine compounds have one or more double bonds, or one or more asymmetric centers. Such compounds can occur as racemates, racemic mixtures, single enantiomers, individual diastereomers, diastereomeric mixtures, and cis- or trans- or E- or Z-double bond isomeric forms.

Also within the scope of this invention are a composition containing one or more of the compounds described above for use in treating an IL-12 overproduction-related disorder, and the use of such a composition for the manufacture of a medicament for the just-described use. Other features or advantages of the present invention will be apparent from the following detailed description of several embodiments, and also from the appending claims.

DETAILED DESCRIPTION

The compounds described above can be prepared by methods well known in the art, as well as by the synthetic routes disclosed herein. For example, a triazine compound of this invention (e.g., Compound 1) can be prepared in a stepwise manner by using cyanuric chloride as a starting material and replacing its three chloro groups with various substitutes by the methods described above. Due to the symmetry of cyanuric chloride, the order of displacement is not of particular importance. For example, a chloro group of cyanuric chloride can be substituted with a nucleophile X—$R_1$—H, wherein X is O or S, thus forming an ether linkage. In another example, a compound of formula (I), wherein Y is $CH_2$ (e.g., Compound 7), can be prepared by reacting the cyanuric chloride with a Grignard reagent, an organotin reagent, an organoboric acid, an organocopper reagent or an organozinc reagent in the presence of an organopalladium compound as a catalyst. If preferred, other types of linkages can be prepared by similar nucleophilic reactions. Sensitive moieties on the triazinyl intermediates and on the nucleophiles can be protected prior to coupling. For suitable protecting groups, see, e.g., Greene (1981) *Protective Groups in Organic Synthesis*, John Wiley & Sons, Inc., New York. A triazine compound thus synthesized can be further purified by flash column chromatography, high performance liquid chromatography, or crystallization.

Also within the scope of this invention is a pharmaceutical composition that contains an effective amount of at least one triazine compound of this invention and a pharmaceutically acceptable carrier. Further, the present invention covers a method of administering an effective amount of one or more triazine compounds described in the "Summary" section to a subject in need of treatment of IL-12 overproduction related diseases (e.g., rheumatoid arthritis, sepsis, or Crohn's disease, multiple sclerosis, psoriasis, or insulin-dependent diabetes mellitus). "An effective amount" refers to the amount of the compound which is required to confer a therapeutic effect on the treated subject. The interrelationship of dosages for animals and humans (based on milligrams per meter squared of body surface) is described in Freireich et al., (1966) *Cancer Chemother Rep* 50: 219. Body surface area may be approximately determined from height and weight of the patient. See, e.g., Scientific Tables, Geigy Pharmaceuticals, Ardley, N.Y., 1970, 537. An effective amount of the compound of this invention can range from about 0.001 mg/Kg to about 1000 mg/Kg. Effective doses will also vary, as recognized by those skilled in the art, depending on the diseases treated, route of administration, excipient usage, and the possibility of co-usage with other therapeutic treatments such as use of other agents.

To practice the method of the present invention, a triazine compound, as a component of a pharmaceutical composition, can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A sterile injectable composition, for example, a sterile injectable aqueous or oleaginous suspension, can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation. A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. A triazine compound can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form specific, more soluble complexes with the compounds of this invention, or one or more solubilizing agents, can be utilized as pharmaceutical excipients for delivery of a triazine compound. Examples of other carriers include colloidal silicon dioxide, magnesium stearate, cellulose, sodium lauryl sulfate, and D&C Yellow # 10.

The biological activities of a triazine compound can be evaluated by a number of cell-based assays. One of such assays can be conducted using cells from human peripheral blood cells (PBMC) or human monocytic cell line (THP-1). The cells are stimulated with a combination of human interferon-γ and lipopolysaccharide or a combination of IFNγ and *Staphylococcus aureus* Cowan I in the presence of a test compound. The level of inhibition of IL-12 production can be measured by determining the amount of p70 by using a sandwich ELISA assay with anti-human IL-12 antibodies. $IC_{50}$ of the test compound can then be determined. Specifically, PBMC or THP-1 cells are incubated with the test compound. Cell viability was assessed using the bioreduction of MTS [3-(4,5-dimethylthiazol-2-yl)-5-(3-carboxymethoxyphenyl)-2-(4-sulfophenyl)-2H-tetrazolium] (Promega, Madison, Wis.).

A triazine compound can also be evaluated by animal studies. For example, one of such studies involves the ability of a test compound to treat adjuvant arthritis (i.e., a IL-12 overproduction related disorder) in rats.

Without further elaboration, it is believed that the above description has adequately enabled the present invention. The following specific embodiments are, therefore, to be construed as merely illustrative, and not limitative of the remainder of the disclosure in any way whatsoever. All of the publications cited herein are hereby incorporated by reference in their entirety.

EXAMPLE 1

Preparation of Compound 1 : N-(1H-indol-3-ylmethylene)-N'-[4-morpholin-4-yl-6-(2-pyridin-2-yl-ethoxy)-[1,3,5]triazin-2-yl]-hydrazine Cyanuric chloride (13.66 g, 74 mmol) was dissolved in methylene chloride (100 mL) at −78° C., followed by the addition of diisopropylethylamine (12.9 mL, 74 mmol). The reaction mixture was stirred for 5 minutes. Morpholine (6.46 mL, 74 mmol) was added dropwise into the reaction mixture in 10 min. The resulting white precipitate was filtered, washed with water, and dried to afford the desired intermediate in quantitative yield (17 g, 100%).

2-(2-Hydroxyethyl)pyridine (2 g, 16.2 mmol) was dissolved in THF (20 mL) at 0° C. 6.5 mL of 2.5 M n-butyl lithium (16.2 mmol) was added into the pyridine solution dropwise in 5 min. The resulting solution was then added dropwise via cannula to a triazine dichloride solution (3.8 g, 16.2 mmol, in THF) at −78° C. The reaction was allowed to warm to room temperature for overnight to yield the triazine monochloride intermediate (2.8 g, 54%) as a white powder. Hydrazine (0.5 mL, 15.5 mmol) was dissolved in 10 mL ethanol at room temperature. The triazine monochloride intermediate (1 g, 3.11 mmol) was added to a solution of ethanol (20 mL) and heated to 60° C. before adding into the hydrazine solution. After stirring for 30 min, white crystals precipitated, which were then filtered, washed with water and air dried to yield the triazine hydrazine intermediate (781 mg, 78%) as a white powder.

Indole-3-aldehyde (1.05 g, 7.25 mmol) and the triazine hydrazine intermediate (2.3 g, 7.25 mmol) were added to 30 mL of methanol at room temperature. 5 mL of acetic acid was added to the reaction mixture and was refluxed for 5 min. Upon cooling, a white precipitate was formed, which was filtered and washed with water to yield Compound 1 as a white powder (1.7 g, 52%).

$^1$H NMR (CDCl$_3$), δ (ppm): 3.28 (t, J=6.9, 2H); 3.7 (broad s, 4H); 3.86 (broad s, 4H); 4.73 (broad t, 2H); 7.14–7.24 (m, 2H); 7.27–7.30 (m, 3H); 7.37 (d, J=8.1, 1H); 7.45 (d, J=2.4, 1H); 7.59 (t, J=7.5, 1H); 8.14 (s, 1H); 8.42 (d, J=7.8, 1H); 8.49 (s, 1H); and 8.56 (d, J=8.5, 1H). MS (ESI): m/z 445.2 (M+H).

EXAMPLE 2

Preparation of Compound 2: 2,3-dimethyl-1H-indol-5-yl)-[4-morpholin-4-yl-6-(2-pyridin-2-yl-ethoxy)-[1,3,5]triazin-2-yl]-amine To a solution of cyanuric chloride (0.922 g, 5.00 mmol, 1.00 equiv.) in 15 mL CH$_2$Cl$_2$ at 0° C. was added slowly DIPEA (1.422 g, 11.00 mmol, 2.20 equiv.) during a period of 10 minutes. Ice bath was removed, and 2-(2-hydroxyethyl)pyridine (0.677 g, 5.50 mmol, 1.10 equiv.) was added, and the reaction mixture was stirred at room temperature for 15 minutes. 5-Amino-2, 3-dimethylindole (0.641 g, 4.00 mmol, 0.80 equiv.) was then added, and stirred for 4 hours at room temperature. A light brown solid precipitated out after 10 mL of water was added to the reaction mixture and stirred for about 10 minutes. The light brown solid was collected by filtration, washed with 2×10 mL water, 5 mL EtOAc and dried (1.50 g, 3.80 mmol, 95%). This solid was then added to a solution of morpholine (0.827 g, 9.5 mmol, 2.50 equiv.) in 30 mL THF, and stirred at 60° C. for 4 hours. Usual workup and flash chromatography purification gave Compound 2 as an off-white solid (1.30 g, 2.92 mmol, 77%).

$^1$H NMR (300 MHz, DMSO-d$_6$), δ ppm: 10.50 (s, 1H); 9.29 (br s, 1H); 8.51 (d, J=4.8 Hz, 1H); 7.70–7.79 (m, 2H); 7.22–7.34 (m, 2H); 7.10 (s, 2H); 4.63 (t, J=6.9 Hz, 2H); 3.71 (br s, 4H); 3.63 (br s, 4H); 3.16 (t, J=6.9 Hz, 2H); 2.78 (s, 3H), 2.07 (br s, 3H); MS (ESI): m/z 446.2 (M+H)$^+$.

EXAMPLE 3

Preparation of Compound 3: N-(1H-indol-3-ylmethylene)-N'-[4-morpholin-4-yl-6-(2-pyridin-3-yl-ethoxy)-[1,3,5]triazin-2-yl]-hydrazine Compound 3 was prepared in a similar manner as described in Example 1.

$^1$H NMR (300 MHz, CDCl$_3$), δ ppm: 9.10 (br s, 1H); 8.55 (d, J=1.8 Hz, 1H); 8.47–8.49 (m, 2H); 8.34–8.41 (m, 1H); 8.07 (s, 1H); 7.60 (dt, J=1.8 Hz, .7.5Hz, 1H); 7.34–7.39 (m, 2H); 7.14–7.25 (m, 3H); 4.58 (br s, 2H); 3.86 (br s, 4H); 3.75 (br s, 4H); 3.09 (t, J=7.2 Hz, 1H); MS (ESI): m/z 445.1 (M+H)$^+$.

EXAMPLE 4

Preparation of Compound 4: N-(3-Methoxy-benzylidene)-N'-[4-morpholin-4-yl-6-(2-pyridin-2-yl-ethoxy)-[1,3,5]triazin-2-yl]-hydrazine Compound 4 was prepared in a similar manner as described in Example 1.

$^1$H NMR (300 MHz, DMSO-d$_6$), δ ppm: 11.19 (s, 1H); 8.52 (dd, J=3.9 Hz, 0.9 Hz, 1H); 8.07 (s, 1H); 7.73 (m, 1H); 7.19–7.36 (m, 4H); 6.95 (dd, J=7.8 Hz, 2.4 Hz, 1H); 4.64 (t, J=6.3 Hz, 2H); 3.64–3.78 (m, 11H); 3.17 (t, J=6.3 Hz, 2H); MS (ESI): m/z 436.2 (M+H)$^+$.

Example 5

Preparation of Compound 5: N-(3-methyl-benzylidene)-N'-[4-morpholin-4-yl-6-(2-pyridin-2-yl-ethoxy)-[1,3,5]triazin-2-yl]-hydrazine Compound 5 was prepared in a similar manner as described in Example 1.

$^1$H NMR (300 MHz, DMSO-d$_6$), δ ppm: 11.14 (s, 1H); 8.52 (dd, J=3.9 Hz, 0.9 Hz, 1H); 8.07 (s, 1H); 7.73 (m, 1H); 7.17–7.45 (m, 6H); 4.64 (t, J=6.3 Hz, 2H); 3.63–3.73 (m, 8H); 3.17 (t, J=6.3 Hz, 2H); 2.33 (s, 3H); MS (ESI): m/z 420.2 (M+H)$^+$.

EXAMPLE 6

Preparation of Compound 6: 4-{4-[N'-(1H-indol-3-ylmethylene)-hydrazinol-]6-morpholin-4-yl-[1,3,5]triazin-2-yl}-butan-1-ol Compound 6 was prepared in a similar manner as described in Example 7.

$^1$H NMR (300 MHz, CDCl$_3$ + DMSO-d$_6$, 8:1), δ ppm: 10.16 (br s, 1H); 9.17 (br s, 1H); 8.37–8.47 (m, 1H); 8.21 (s, 1H); 7.36–7.47 (m, 3H); 7.17–7.26 (m, 2H); 3.93 (br s, 4H); 3.77(br s, 4H); 3.65 (t, J=6.3 Hz, 2H); 2.62 (br s, 2H); 1.84–1.92 (m, 2H); 1.62–1.71 (m, 2H); MS (ESI): m/z 396.2 (M+H)$^+$.

EXAMPLE 7

Preparation of Compound 7: N-{4-[3-(3,4-dimethoxy-phenyl)-propyl]-6-morpholin-4-yl-1,3,5-triazin-2-yl}-N'-[1-(1H-indol-3-yl)-meth-(E)-ylidene]-hydrazine To a solution of 3-(3,4-dimethoxyphenyl)-propyl iodide (1.224 g, 4.00 mmol, 1.00 equiv.) in 20 mL dry THF was added highly active zinc (suspension in THF, Rieke metal from Aldrich, 5.2 mL 0.05 g/mL, 4.00 mmol, 1.00 equiv.). The mixture was stirred at room temperature overnight. 2,4-dichloro-6-morpholin-4-yl-1,3,5-triazine (0.936 g, 4.0 mmol, 1.00 equiv.) and trans-benzyl-(chloro)-bis-(triphenylphosphine)palladium(II) (0.03 g, 0.04 mmol, 0.01 equiv.) were added, and the reaction mixture was stirred at room temperature for 8 hours. Usual workup and flash chromatography purification gave 4-chloro-2-[3-(3,4-dimethoxyphenyl)propyl]-6-morpholin-4-yl-1,3,5-triazine as a light yellow solid which was treated with hydrazine following the typical procedure to yield {4-[3-(3,4-Dimethoxy-phenyl)-propyl]-6-morpholin-4-yl-1,3,5-triazin-2-yl}-hydrazine as a white solid (0.85 g, 2.27 mmol, 57%). MS (ESI): m/z 375.2 (M+H)$^+$.

A mixture of {4-[3-(3,4-dimethoxy-phenyl)-propyl]-6-morpholin-4-yl-1,3,5-triazin-2-yl}-hydrazine (0.75 g, 2.00 mmol, 1.00 equiv.), indole-3-carboxaldehyde (0.29 g, 2.00 mmol, 1.00 equiv.), and AcOH (80 mg, cat.) in 15 mL MeOH was stirred at 75° C. for 4 hours. Solvent was removed and the residue was subjected to flash chromatography purification and crystallization in MeOH to yield Compound 7 as an off-white solid (0.72 g, 1.44 mmol, 72%).

$^1$H NMR (300 MHz, CDCl$_3$), δ ppm: 8.57 (br s, 1H); 8.45 (br s, 1H); 8.29–8.32 (m, 1H); 8.00 (s, 1H); 7.39–7.43 (m, 2H); 7.23–7.34 (m, 2H); 6.74–6.80 (m, 3H); 6.30 (s, 1H); 3.86 (s, 3H); 3.85 (s, 3H); 3.78–3.84 (m, 4H); 3.67–3.70 (m, 4H); 2.63–2.71 (m, 4H), 2.03–2.13 (m, 2H); MS (ESI): m/z 502.2 (M+H)$^+$.

EXAMPLE 8

Preparation of Compound 8: N-{4-[2-(2,2-Dimethyl-[1,3]dioxolan-4-yl)-ethoxy]-6-morpholin-4-yl-[1,3,5]triazin-2-yl}-N'-(1H-indol-3-ylmethylene)-hydrazine Compound 8 was prepared in a similar manner as described in Example 1.

$^1$H NMR (300 MHz, CD$_3$Cl) δ (ppm): 8.50 (s, 1H), 8.42 (d, J=8.4Hz, 1H), 8.24 (s, 1H), 8.09 (s, 1H), 7.44 (d, J=3.0Hz, 1H), 7.38 (d, 1H, J=7.2Hz), 7.20–7.26 (m, 2H), 4.55 (br., 2H), 4.28(d, J=7.4Hz, 1H) 3.84 (m, 4H), 3.71 (m, 4H), 3.60 (t, J=7.4Hz, 2H), 2.03 (m, 2H), 1.42 (s, 3H), 1.35 (s, 3H). MS (ESI): m/z 468.3 (M+H)$^+$.

EXAMPLE 9

Preparation of Compound 9: N-[4-(4,5-dihydro-oxazol-2-ylmethoxy)-6-morpholin-4-yl-[1,3,5]triazin-2-yl]-N'-(1H-indol-3-ylmethylene)-hydrazine Compound 9 was prepared in a similar manner as described in Example 1.

$^1$H NMR (300 MHz, DMSO-d$_6$) δ (ppm): 11.40 (s, 1H), 10.91 (s, 1H), 8.32–8.28 (m, 2H), 7.68 (bs,1H), 7.40–7.37 (m, 1H), 7.21–7.05 (m, 2H), 4.80–4.66 (m, 4H), 3.75–3.55 (m, 8H), 3.15 (s, 2H); MS (ESI): m/z 423.1.

EXAMPLE 10

Preparation of Compound 10: {4-[N'-(1H-indol-3-ylmethylene)-hydrazino]-6-morpholin-4-yl-[1,3,5]triazin-2-yloxy}-acetic acid ethyl ester Compound 10 was prepared in a similar manner as described in Example 1.

$^1$H NMR (300 MHz, DMSO-d$_6$) δ (ppm): 8.62–8.60 (m, 1H), 8.42(d, 1H, J=9.0 Hz), 8.09 (s, 1H), 7.45 (bs, 1H), 7.39–7.36 (m, 1H), 7.28–7.20 (m, 3H), 4.84 (s, 2H), 4.27–4.19 (m, 2H), 3.80–3.65 (m, 8H), 1.25 (t, 3H, J=7.2 Hz); MS (ESI): m/z 426.1.

EXAMPLE 11

Preparation of Compound 11: N-(2-hydroxy-ethyl)-2-{4-[N'-(1H-indol-3-ylmethylene)-hydrazino]-6-morpholin-4-yl-[1,3,5]triazin-2-yloxy}-acetamide Compound 11 was prepared in a similar manner as described in Example 1.

$^1$H NMR (DMSO-d$_6$) δ (ppm): 11.40 (s, 1H), 10.92 (s, 1H), 8.32–8.28 (m, 2H), 8.00–7.93 (m, 1H), 7.69 (bs, 1H),7.40–7.37 (m, 1H), 7.21–7.05 (m, 2H), 4.75–4.60 (m, 4H), 3.75–3.55 (m, 8H), 3.20–3.10 (m, 2H); MS (ESI): m/z 441.1.

EXAMPLE 12

Preparation of Compound 12: 4-[4-(2,3-Dimethyl-1H-indol-5-ylamino)-6-morpholin-4-yl-[1,3,5]triazin-2-yloxy]-benzonitrile Compound 11 was prepared in a similar manner as described in Example 2.

$^1$H-NMR (300 MHz, DMSO-d$_6$), δ (ppm): 1.93 (s, 1H), 2.08 (s, 2H), 2.27 (s,3H), 3.74–3.27 (m, 8H), 6.99 (s, 1H), 7.09 (s, 1H), 7.46 (d, J=8.7 Hz), 7.79 (s, 1H), 7.91 (d, J=8.7 Hz), 9.46 (s, 1H), 10.51 (s, 1H). MS (ESI): m/z 441.2 (M+H)$^+$.

EXAMPLE 13

In Vitro Assays

Reagents. *Staphylococcus aureus* Cowan I (SAC) was obtained from Calbiochem (La Jolla, Calif.), and lipopolysaccharide (LPS, *Serratia marscencens*) was obtained from Sigma (St. Louis, Mo.). Human and mouse recombinant IFNγ were purchased from Boehringer Mannheim (Mannheim, Germany) and Pharmingen (San Diego, Calif.), respectively.

Human In Vitro Assay. Human PBMC were isolated by centrifugation using Ficoll-Paque (Pharmacia Biotech, Uppsala, Sweden) and prepared in RPMI medium supplemented with 10% fetal calf serum (FCS), 100 U/mL penicillin, and 100 µg/mL streptomycin. PBMC were plated in wells of a 96-well plate at a concentration of 5×10$^5$ cells/well, and primed by adding IFNγ (30 U/mL) for 22 h and stimulated by adding LPS (1 µg/mL), or by adding IFNγ (100 U/mL) and then stimulated by adding SAC (0.01%). A test compound was dissolved in DMSO, and added to wells of the 96 well plate. The final DMSO concentration was adjusted to 0.25% in all cultures, including the compound-free control. Human THP-1 cells were plated in wells, primed by adding IFNγ (100 U/mL) for 22 h and stimulated by adding SAC (0.025%) in the presence of different concentrations of the test compound. Cell-free supernatants were taken 18 h later for measurement of cytokines. Cell viability was assessed using the bioreduction of MTS. Cell survival was estimated by determining the ratio of the absorbance in compound-treated groups versus compound-free control.

The supernatant was assayed for the amount of IL-12p40, IL-12p70, or IL-10 by using a sandwich ELISA with anti-human antibodies, i.e., a Human IL-12 p40 ELISA kit from R&D Systems (Berkeley, Calif.), and a Human IL-12 p70 or IL-10 ELISA kit from Endogen (Cambridge, Mass.). Assays were based on the manufacturer's instructions.

Murine In Vitro Assay. Balb/c mice (Taconic, Germantown, N.Y.) were immunized with *Mycobacterium tuberculosis* H37Ra (Difco, Detroit, Mich.) The splenocytes were harvested 5 days and prepared in RPMI medium supplemented with 10% FCS and antibiotics in a flat bottom 96-well plate with 1×10$^6$ cells/well. The splenocytes were then stimulated with a combination of IFNγ (60 ng/mL) and SAC (0.025%) [or LPS (20 µg/mL)] in the presence of a test compound. Cell-free supernatants were taken 24 h later for the measurement of cytokines. The preparation of compound and the assessment of cell viability were carried out as described above. Mouse IL-12 p70, IL-10, IL-1β, and TNFα were measured using ELISA kits from Endogen, according to the manufacturer's instructions.

The biological activities of triazine compounds were tested on human PBMC or THP-1 cells. At least 240 compounds have IC$_{50}$ values of at least 5 µM. Unexpectedly, some of the test compounds have IC$_{50}$ values as low as <1 nM.

EXAMPLE 14

In Vivo Assays

Treatment of Adjuvant Arthritis in Rats: Adjuvant arthritis (AA) was induced in female Lewis rats by the intracutaneous injection (base of the tail) of 0.1 mL of a 10 mg/mL bacterial suspension made from ground, heat-killed *Mycobacterium tuberculosis* H37Ra suspended in incomplete Freund's adjuvant. Rats were given a test compound orally once a day for 12 days, starting the day following the induction. The development of polyarthritis was monitored daily by macroscopic inspection and assignment of an arthritis index to each animal, during the critical period (days 10 to 25 post-immunization).

The intensity of polyarthritis was scored according to the following scheme: (a) Grade each paw from 0 to 3 based on erythema, swelling, and deformity of the joints: 0 for no erythema or swelling; 0.5 if swelling is detectable in at least one joint; 1 for mild swelling and erythema; 2 for swelling and erythema of both tarsus and carpus; and 3 for ankylosis and bony deformity. Maximum score for all 4 paws was thus 12. (b) Grade for other parts of the body: for each ear, 0.5 for redness and another 0.5 if knots are present; 1 for connective tissue swelling (saddle nose); and 1 for the presence of knots or kinks in the tail. The highest possible arthritic index was 16.

Experiments with the AA model were repeated four times. Oral administration of triazine compounds described above (e.g., Compounds 1 and 2 reproducibly reduced the arthritic score and delayed the development of polyarthritis in a dose-dependent manner. The arthritis score used in this model was a reflection of the inflammatory state of the structures monitored and the results therefore show the ability of the test compound to provide relief for this aspect of the pathology.

Treatment of Crohn's disease in dinitrobenzene sulfonic acid-induced inflammatory bowel syndrome model rats: Wistar derived male or female rats weighing 200 ±20 g and fasted for 24 hours were used. Distal colitis was induced by intra-colonic instillation of 2,4-dinitrobenzene sulfonic acid (DNBS, 25 mg in 0.5 mL ethanol 30%) after which air (2 mL) was gently injected through the cannula to ensure that the solution remained in the colon. A test compound and/or vehicle was administered orally 24 and 2 hours before DNBS instillation and then daily for 5 days. One control group was similarly treated with vehicle alone while the other is treated with vehicle plus DNBS. The animals were sacrificed 24 hours after the final dose of test compound administration and each colon was removed and weighed. Colon-to-body weight ratio was then calculated for each animal according to the formula: Colon (g)/BW×100. The "Net" increase in ratio of Vehicle-control+DNBS group relative to Vehicle-control group was used as a base for comparison with test substance treated groups and expressed as "% Deduction." Triazine compounds described above (e.g., Compounds 1 and 2 reproducibly had about 30% deduction. A 30% or more reduction in colon-to-body weight ratio, relative to the vehicle treated control group, was considered significant.

Rats treated with test substance orally showed a marked reduction in the inflammatory response. These experiments were repeated three times and the effects were reproducible.

Treatment of Crohn's disease in $CD4^+CD45Rb^{high}$ T cell-reconstituted SCID colitis model mice:

Spleen cells were prepared from normal female BALB/c mice. For cell purification, the following anti-mouse antibodies were used to label non-$CD4^+$T cells: B220 (RA3-6B2), CD11b (M1/70), and CD8α(53-6.72). All antibodies were obtained from BioSource (Camarillo, Calif.). M450 anti-rat IgG-coated magnetic beads (Dynal, Oslo, Norway) were used to bind the antibodies and negative selection was accomplished using an MPC-1 magnetic concentrator. The enriched $CD4^+$cells were then labeled for cell sorting with FITC-conjugated CD45RB (16A, Pharmingen, San Diego, Calif.) and PE-conjugated CD4 (CT-CD4, Caltag, Burlingame, Calif.). $CD4^+CD45RB^{high}$ cells were operationally defined as the upper 40% of CD45Rb-staining $CD4^+$cells and sorted under sterile conditions by flow cytometry. Harvested cells were resuspended at $4\times10^6$/mL in PBS and injected 100 μL intraperitoneally into female C.B-17 SCID mice. Triazine compounds described above (e.g., Compounds 1 and 2) and/or vehicle was orally administered once a day for 5 days per week, starting the day following the transfer. The transplanted SCID mice were weighed weekly and their clinical condition was monitored.

Colon tissue samples were fixed in 10% buffered formalin and embedded in paraffin. Sections (4 μm) collected from ascending, transverse, and descending colon were cut and stained with hematoxylin and eosin. The severity of colitis was determined based on histological examination of the distal colon sections, whereby the extent of colonic inflammation was graded on a scale of 0–3 in each of four criteria: crypt elongation, cell infiltration, depletion of goblet cells, and the number of crypt abscesses.

LP lymphocytes were isolated from freshly obtained colonic specimens. After removal of payer's patches, the colon was washed in Ca/Mg-free HBSS, cut into 0.5 cm pieces and incubated twice in HBSS containing EDTA (0.75mM), DTT (1 mM), and antibiotics (amphotericin 2.5 μg/mL, gentamicin 50 μg/mL from Sigma) at 37° C. for 15 min. Next, the tissue was digested further in RPMI containing 0.5 mg/mL collagenase D, 0.01 mg/mL DNase I (Boehringer Manheim), and antibiotics at 37° C. LP cells were then layered on a 40–100% Percoll gradient (Pharmacia, Uppsala, Sweden), and lymphocyte-enriched populations were isolated from the cells at the 40–100% interface.

To measure cytokine production, 48-well plates were coated with 10 μg/mL murine anti-CD3ε antibody (145-2C11) in carbonate buffer (PH 9.6) overnight at 4° C. $5\times10^5$ LP cells were then cultured in 0.5ml of complete medium in precoated wells in the presence of 1 μg/mL soluble anti-CD28 antibody (37.51). Purified antibodies were obtained from Pharmingen. Culture supernatants were removed after 48 h and assayed for cytokine production. Murine IFNγ was measured using an ELISA kit from Endogen (Cambridge, Mass.), according to the manufacturer's instructions.

Histological analysis showed that oral administration of triazine compounds described above (e.g., Compounds 1 and 2 reduced colonic inflammation as compared to vehicle control. The suppressive effect was dose-dependent with a substantial reduction at a dose of 10 mg/kg. The calculated colon-to-body weight ratio was consistent with the histological score, showing attenuation by treatment with the test compound. Furthermore, analysis of cytokines from LP cells in response to anti-CD3 antibody and anti-CD28 antibody demonstrated that LP cells from vehicle control produced an augmented level of IFNγ and treatment with test substance greatly diminished the production. These results clearly demonstrated the potential of the test substance in treatment of inflammatory bowel disease represented by Crohn's disease.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous a triazine compound described in the specification also can be made, screened for their inhibiting IL-12 activities, and used to practice this invention. Thus, other embodiments are also within the claims.

What is claimed is:

1. A method for treating an interleukin-12 overproduction-related disorder, wherein the disorder is rheumatoid arthritis, sepsis, Crohn's disease, multiple sclerosis, psoriasis, or insulin-dependent diabetes mellitus, comprising administering to a subject in need thereof the compound of formula (I):

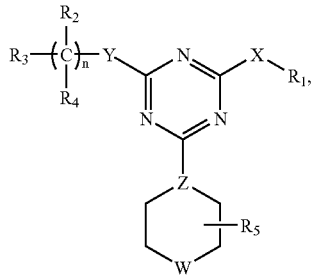

wherein
$R_1$ is

aryl, or heteroaryl;
each of $R_2$, $R_4$, and $R_5$, independently, is $R^c$, halogen, nitro, nitroso, cyano, azide, isothionitro, $SR^c$, or $OR^c$;
$R_3$ is $R^c$, alkenyl, alkynyl, aryl, heteroaryl, cyclyl, heterocyclyl, $OR^c OC(O)R^c$, $SO_2R^c$, $S(O_2)R^c$, $S(O_2)NR^c R^d$, $SR^c$, $NR^cR^d$, $NR^cCOR^d$, $NR^cC(O)OR^d$, $NR^cC(O)NR^cR^d$, $NR^cSO_2R^d$, $COR^c$, $C(O)OR^c$ or $C(O)NR^cR^d$;
n is 0, 1, 2, 3, 4, 5, 6, or 7;
X is O, S, S(O), S(O$_2$), or NR$^c$;
Y is a covalent bond, CH$_2$, C(O), C=N—R$^c$, C=N—OR$^c$, C=N—SR$^c$, O, S, S(O), S(O$_2$), or NR$^c$.
Z is N or CH; and
W is O, S, S(O), S(O$_2$), NR$^c$, or NC(O)R$^c$;
in which each of $R^a$ and $R^b$, independently, is H, alkyl, aryl, heteroaryl; and each of $R^c$ and $R^d$, independently, is H, alkyl, or alkylcarbonyl; or a pharmaceutically acceptable salt thereof.

2. The method of claim 1, wherein the disorder is rheumatoid arthritis.

3. The method of claim 1, wherein the disorder is Crohn's disease.

4. The method of claim 1, wherein the disorder is multiple sclerosis.

5. The method of claim 1, wherein the disorder is psoriasis.

6. The method of claim 1, wherein the disorder is diabetes mellitus.

7. The method of claim 1, wherein the disorder is sepsis.

8. A pharmaceutical composition comprising the compound of formula (I):

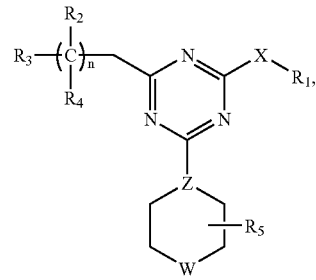

wherein
$R_1$ is

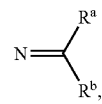

aryl, or heteroaryl;
each of $R_2$, $R_4$, and $R_5$, independently, is $R^c$, halogen, nitro, nitroso, cyano, azide, isothionitro, $SR^c$, or $OR^c$;
$R_3$ is $R^c$, alkenyl, alkynyl, aryl, heteroaryl, cyclyl, heterocyclyl, $OR^c$, $OC(O)R^c$, $SO_2R^c$, $S(O_2)R^c$, $S(O_2)NR^c R^d$, $SR^c$, $NR^cR^d$, $NR^cCOR^d$, $NR^cC(O)OR^d$, $NR^cC(O)NR^cR^d$, $NR^cSO_2R^d$, $COR^c$, $C(O)OR^c$, or $C(O)NR^cR^d$;
n is 0, 1, 2, 3, 4, 5, 6, or 7;
X is O, S, S(O), S(O$_2$), or NR$^c$,
Y is a covalent bond, CH$_2$, C(O), C=N—R$^c$, C=N—OR$^c$, C=N—SR$^c$, (O), S, S(O), S(O$_2$), or NR$^c$;
Z is N or CH; and
W is O, S, S(O), S(O$_2$), NR$^c$, or NC(O)R$^c$;
in which each of $R^a$ and $R^b$, independently, is H, alkyl, aryl, heteroaryl; and each of $R^c$ and $R^d$, independently, is H, alkyl, or alkylcarbonyl; or a pharmaceutically acceptable salt thereof; and a pharmaceutically acceptable carrier.

9. The pharmaceutical composition of claim 8, wherein $R_1$ is

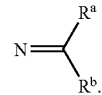

10. The pharmaceutical composition of claim 9, wherein W is O.

11. The pharmaceutical composition of claim 10, wherein $R_5$ is H or alkyl.

12. The pharmaceutical composition of claim 9, wherein X is NR$^c$.

13. The pharmaceutical composition of claim 12, wherein R$^c$ is H, methyl, ethyl, or acetyl.

14. The pharmaceutical composition of claim 9, wherein Y is O or CH$_2$, and n is 0, 1, 2, 3, or 4.

15. The pharmaceutical composition of claim 14, wherein $R_3$ is aryl or heteroaryl.

16. The pharmaceutical composition of claim 15, wherein $R_3$ is pyridinyl.

17. The pharmaceutical composition of claim 14, wherein $R_3$ is $OR^c$, $SR^c$, $C(O)OR^c$, or $C(O)NR^cR^d$.

18. The pharmaceutical composition of claim 14, wherein $R_3$ is

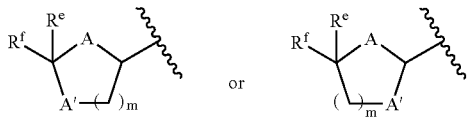

in which each of A and A', independently, is O, S, or NH; each of $R^e$ and $R^f$, independently is H, alkyl, aryl, or heteroaryl; and
m is 1 or 2.

19. The pharmaceutical composition of claim 9, wherein one of $R^a$ and $R^b$ is

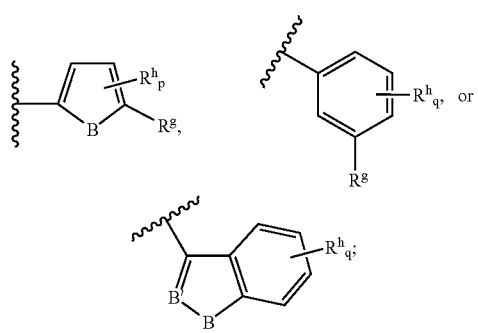

in which
B is $NR^i$, O, or S;
B' is N or $CR^i$;
$R^g$ is H, alkyl, or alkoxyl;
$R^h$ is halogen, CN, hydroxyl, alkyl, aryl, heteroaryl, alkoxyl, aryloxyl, or heteroaryloxyl;
$R^i$ is H, alkyl, or alkylcarbonyl;
p is 0, 1, or 2; and
q is 0, 1, 2, 3, or 4.

20. The pharmaceutical composition of claim 19, wherein one of $R^a$ and $R^b$ is

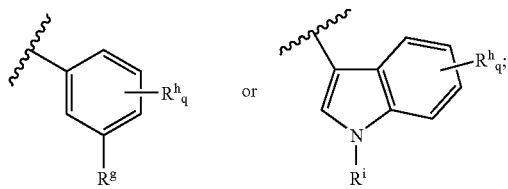

and the other of $R^a$ and $R^b$ is alkyl.

21. The pharmaceutical composition of claim 20, wherein $R^g$ is H, methyl, ethyl, methoxy, or ethoxy; $R^h$ is F, Cl, CN, methoxy, methyl, or ethoxy; $R^i$ is H, methyl, ethyl, or acetyl, and q is 0, 1, or 2.

22. The pharmaceutical composition of claim 21, wherein $R^g$ is methyl or methoxy; $R^i$ is H; and q is 0.

23. The pharmaceutical composition of claim 21, wherein W is O; and $R_5$ is H or alkyl.

24. The pharmaceutical composition of claim 23, wherein X is $NR^c$; and $R^c$ is H, methyl, ethyl, or acetyl.

25. The pharmaceutical composition of claim 24, wherein Y is O or $CH_2$; and n is 0, 1, 2, 3, or 4.

26. The pharmaceutical composition of claim 25, wherein $R_3$ is aryl or heteroaryl.

27. The pharmaceutical composition of claim 26, wherein $R_3$ is pyridinyl.

28. The pharmaceutical composition of claim 21, wherein Y is O or $CH_2$, and n is 0, 1, 2, 3, or 4.

29. The pharmaceutical composition of claim 28, wherein $R_3$ is aryl or heteroaryl.

30. The pharmaceutical composition of claim 29, wherein $R_3$ is pyridinyl.

31. The pharmaceutical composition of claim 8, wherein $R_1$ is aryl or heteroaryl.

32. The pharmaceutical composition of claim 30, wherein $R_1$ is

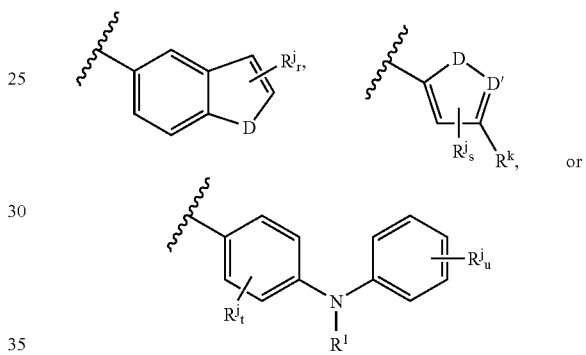

in which D is O, S, or $NR^m$;
D' is N or $CR^m$;
$R^j$ is halogen, CN, hydroxyl, alkyl, aryl, heteroaryl, alkoxyl, aryloxyl, or heteroaryloxyl;
$R^k$ is aryl or heteroaryl;
$R^l$ is H, alkyl, or alkylcarbonyl;
$R^m$ is H, alkyl, or alkylcarbonyl;
r is 0, 1, or 2;
s is 0 or 1;
t is 0, 1, 2, 3, or 4; and
u is 0, 1, 2, 3, 4, or 5.

33. The pharmaceutical composition of claim 32, wherein X is $NR^c$; and $R^c$ is H, methyl, ethyl, or acetyl.

34. The pharmaceutical composition of claim 33, wherein W is O; and $R_5$ is H or alkyl.

35. The pharmaceutical composition of claim 34, wherein Y is O or $CH_2$; and n is 0, 1, 2, 3, or 4.

36. The pharmaceutical composition of claim 32, wherein Y is O or $CH_2$; and n is 0, 1, 2, 3, or 4.

37. The pharmaceutical composition of claim 36, wherein $R_3$ is aryl or heteroaryl.

38. The pharmaceutical composition of claim 37, wherein $R_3$ is pyridinyl.

39. The pharmaceutical composition of claim 36, wherein $R_3$ is $OR^c$, $SR^c$, $C(O)OR^c$ or $C(O)NR^cR^d$.

40. The pharmaceutical composition of claim 36, wherein $R_3$ is

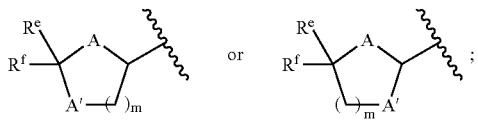

in which each of A and A', independently, is O, S, or NH; each of $R^e$ and $R^f$, independently is H, alkyl, aryl, or heteroaryl; and m is 1 or 2.

41. The pharmaceutical composition of claim 36, wherein $R_1$ is

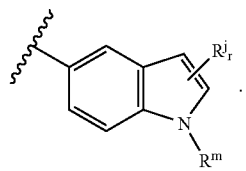

42. The pharmaceutical composition of claim 41, wherein $R^j$ is methyl, ethyl, propyl, or benzyl; and r is 1 or 2.

43. The pharmaceutical composition comprising the compound of formula (I):

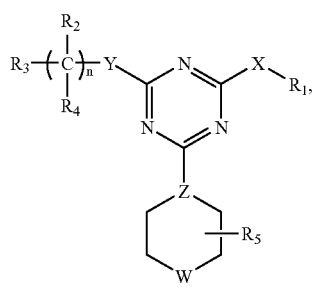

wherein $R_1$ is

aryl, or heteroaryl;

each of $R_2$, $R_4$, and $R_5$, independently, is $R^c$, halogen, nitro, nitroso, cyano, azide, isothionitro, $SR^c$, or $OR^c$;

$R_3$ is $R^c$, alkenyl, alkynyl, aryl, heteroaryl, cyclyl, heterocyclyl, $OR^c$, $OC(O)R^c$, $SO_2R^c$, $S(O_2)R^c$, $S(O_2)NR^c R^d$, $SR^c$, $NR^c R^d$, $NR^c COR^d$, $NR^c C(O)OR^d$, $NR^c C(O)NR^c R^d$, $NR^c SO_2R^d$, $COR^c$, $C(O)OR^c$, or $C(O)NR^c R^d$;

n is 0, 1, 2, 3, 4, 5, 6, or 7;

X is O, S, S(O), $S(O_2)$, or $NR^c$;

Y is a covalent bond, $CH_2$, C(O), C=N—$R^c$, C=N—$OR^c$, C=N—$SR^c$, O, S, S(O), $S(O_2)$, or $NR^c$;

Z is CH; and

W is O, S, S(O), $S(O_2)$, $NR^c$, or $NC(O)R^c$;

in which each of $R^a$ and $R^b$, independently, is H, alkyl, aryl, heteroaryl; and each of $R^c$ and $R^d$, independently, is H, alkyl, or alkylcarbonyl; or a pharmaceutically acceptable salt thereof; and a pharmaceutically acceptable carrier.

44. The pharmaceutical composition of claim 43, wherein $R_1$ is

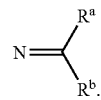

45. The pharmaceutical composition of claim 44, wherein W is O; and $R_5$ is H or alkyl.

46. The pharmaceutical composition of claim 44, wherein X is $NR^c$; and $R^c$ is H, methyl, ethyl, or acetyl.

47. The pharmaceutical composition of claim 44, wherein Y is O or $CH_2$, and n is 0, 1, 2, 3, or 4.

48. The pharmaceutical composition of claim 44, wherein one of $R^a$ and $R^b$ is

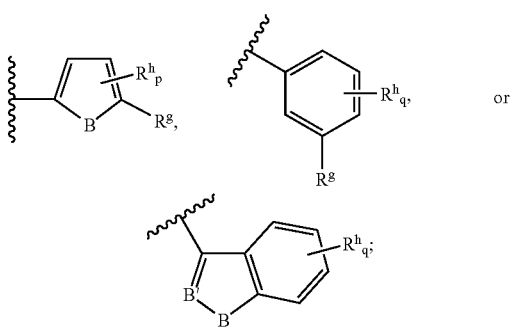

in which B is $NR^i$, O, or S;

B' is N, CH, or $CR^i$;

$R^g$ is H, alkyl, or alkoxyl;

$R^h$ is halogen, CN, hydroxyl, alkyl, aryl, heteroaryl, alkoxyl, aryloxyl, or heteroaryloxyl;

$R^i$ is H, alkyl, or alkylcarbonyl;

p is 0, 1, or 2; and q is 0, 1, 2, 3, or 4.

49. The pharmaceutical composition of claim 43, wherein $R_1$ is aryl or heteroaryl.

50. The pharmaceutical composition of claim 49, wherein W is O; and $R_5$ is H or alkyl.

51. The pharmaceutical composition of claim 49, wherein X is $NR^c$; and $R^c$ is H, methyl, ethyl, or acetyl.

52. The pharmaceutical composition of claim 49, wherein Y is O or $CH_2$; and n is 0, 1, 2, 3, or 4.

53. The pharmaceutical composition of claim 49, wherein $R_1$ is

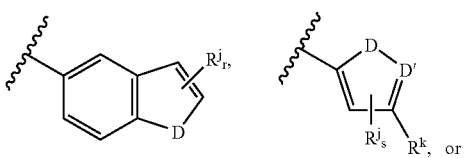

-continued
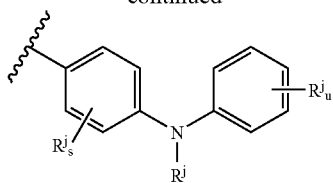
in which D is O, S, or NR$^m$;
D' is N or CR$^m$;
R$^j$ is halogen, CN, hydroxyl, alkyl, aryl, heteroaryl, alkoxyl, aryloxyl, or heteroaryloxyl;
R$^k$ is aryl or heteroaryl;
R$^l$ is H, alkyl, or alkylcarbonyl;
R$^m$ is H, alkyl, or alkylcarbonyl;
r is 0, 1, or 2;
s is 0 or 1;
t is 0, 1, 2, 3, or 4; and
u is 0, 1, 2, 3, 4, or 5.
* * * * *